(12) United States Patent
Chen

(10) Patent No.: US 9,028,827 B2
(45) Date of Patent: *May 12, 2015

(54) COMPOSITIONS AND METHODS FOR TREATING HEPATITIS VIRUS INFECTION

(75) Inventor: David C. P. Chen, Taipei (TW)

(73) Assignee: Asia Hepato Gene Co., Kaohsiung (TW)

( * ) Notice: Subject to any disclaimer, the term of this patent is extended or adjusted under 35 U.S.C. 154(b) by 438 days.

This patent is subject to a terminal disclaimer.

(21) Appl. No.: 13/197,110

(22) Filed: Aug. 3, 2011

(65) Prior Publication Data

US 2012/0034238 A1      Feb. 9, 2012

Related U.S. Application Data

(60) Provisional application No. 61/370,217, filed on Aug. 3, 2010.

(51) Int. Cl.

| | | |
|---|---|---|
| A61K 39/395 | (2006.01) | |
| A61K 39/40 | (2006.01) | |
| A61K 39/42 | (2006.01) | |
| C07K 16/12 | (2006.01) | |
| A61K 36/232 | (2006.01) | |
| A61K 36/258 | (2006.01) | |
| A61K 36/284 | (2006.01) | |
| A61K 36/537 | (2006.01) | |
| A61K 36/748 | (2006.01) | |
| A61K 36/9066 | (2006.01) | |
| A61K 36/9068 | (2006.01) | |
| A61K 39/00 | (2006.01) | |

(52) U.S. Cl.
CPC .............. *C07K 16/121* (2013.01); *A61K 35/57* (2013.01); *A61K 36/232* (2013.01); *A61K 36/258* (2013.01); *A61K 36/284* (2013.01); *A61K 36/537* (2013.01); *A61K 36/748* (2013.01); *A61K 36/9066* (2013.01); *A61K 36/9068* (2013.01); *A61K 39/40* (2013.01); *A61K 2039/505* (2013.01); *C07K 2317/11* (2013.01); *C07K 2317/23* (2013.01)

(58) Field of Classification Search
None
See application file for complete search history.

(56) References Cited

U.S. PATENT DOCUMENTS

| 5,164,195 | A  * | 11/1992 | Lew ............................... 424/490 |
|---|---|---|---|
| 7,780,951 | B2 * | 8/2010 | Ducatelle et al. .............. 424/9.2 |
| 7,854,942 | B2 * | 12/2010 | Sunwoo et al. ................ 424/439 |
| 8,715,671 | B2 * | 5/2014 | Chen et al. ................. 424/157.1 |
| 2009/0194616 | A1 * | 8/2009 | Hiew et al. ....................... 241/23 |

OTHER PUBLICATIONS

O'Farrelly et al. Oral ingestion of egg yolk immunoglobulin from hens immunized with an enterotoxigenic *Escherichia coli* strain prevents diarrhea in rabbits challenged with the same strain. Infect Immun. Jul. 1992;60(7):2593-7.*
Umemura et al. Anti-*Helicobacter pylori* seropositivity: influence on severity and treatment response in patients with chronic hepatitis C. J Viral Hepat. Jan. 2007;14(1):48-54.*
Beck et al. Validation of egg yolk antibody testing as a method to determine influenza status in white leghorn hens. Avian Dis. 2003;47(3 Suppl):1196-9. Abstract Only.*
Shin et al. Use of egg yolk-derived immunoglobulin as an alternative to antibiotic treatment for control of *Helicobacter pylori* infection. Clin Diagn Lab Immunol. Sep. 2002;9(5):1061-6.*
Rollier et al. Control of Heterologous Hepatitis C Virus Infection in Chimpanzees is Associated with the Quality of Vaccine-Induced Peripheral T-Helper Immune Response. J Virol. 2004, 78(1): 187-196.*
Shirai et al. An Epitope in Hepatitis C Virus Core Region Recognized by Cytotoxic T Cells in Mice and Humans. J Virol, 1994, 68(5): 3334-3342.*
Huang et al. Recent development o therapeutics for chronic HCV infection. Antiviral Res 71 (2006) 351-362.*
Tan et al. Strategies for hepatitis C therapeutic intervention: now and next. Curr Opin in Pharmacology, 2004, 4: 465-470.*
Racanelli et al. Presentation of HCV antigens to naive CD8+T cells: why the where, when, what and how are important for virus control and infection outcome. Clin Immunol. Jul. 2007;124(1):5-12.*
Koziel et al. Hepatitis C virus (HCV)-specific cytotoxic T lymphocytes recognize epitopes in the core and envelope proteins of HCV. J Virol. Dec. 1993;67(12):7522-32.*
Berzofsky et al. Progress on new vaccine strategies against chronic viral infections. J Clin Invest. Aug. 2004;114(4):450-62.*

* cited by examiner

*Primary Examiner* — Michelle S Horning
(74) *Attorney, Agent, or Firm* — WPAT, P.C.; Anthony King

(57) ABSTRACT

The present invention relates to a method for treating hepatitis virus infection comprising administering to a subject infected with a hepatitis virus an effective amount of a yolk or yolk antibody obtained from an egg of a fowl which has been immunized using *Helicobacter pylori* as an antigen. In particular, the method is effective in reducing virus titer and/or decreasing a level of glutamic oxaloacetic transaminase (GOT) or glutamic pyruvic transaminase (GPT) in the subject. Also provided is a composition for treating hepatitis virus infection which comprises the yolk or yolk antibody in combination with one or more supplemental ingredients such as Salviae Miltiorrhiza Radix, Oldennlandiae Hb., Zingiberis Radix, Ginseng Radix, Atractylodis Radix, Curcumae Radix, Angelicae Sinensis Radix, bee propolis, calcium lactate, soy proteins, probiotics, and grain bran.

7 Claims, 3 Drawing Sheets

COMPOSITIONS AND METHODS FOR TREATING HEPATITIS VIRUS INFECTION

This application claims the benefit of U.S. Provisional Application No. 61/370,217, filed Aug. 3, 2010, which is incorporated herein by reference in its entirety.

FIELD OF THE INVENTION

The present invention relates to the compositions and methods for treating hepatitis virus infection.

BACKGROUND OF THE INVENTION

Hepatitis viral infection is one of the major causes of hepatitis. Currently, at least 8 different hepatitis viruses including the A, B, C, D, E, F, G and cryptogenic hepatitis viruses, are believed to exist. Of them, hepatitis B virus (HBV, a hepadnavirus) and hepatitis C virus (HCV, a flavivirus) lead to the greatest public health problem in industrialized countries. Hepatitis viral infection is also highly related to liver fibrosis/cirrhosis, liver cancer (hepatocellular carcinoma, HCC), liver failure and death.

In 2006, Chen C J et al. reported after 11.4 years following-up of 3,653 hepatitis B carriers that the incidence of liver cancer is highly related to hepatitis B DNA virus titer (Chen C J et al., Risk of Hepatocellular Carcinoma Across a Biological Gradient of Serum Hepatitis B Virus DNA Level, JAMA. 2006;295(1):65-73.) Therefore, reducing the virus DNA of hepatitis B carriers is the most important issue in management of these patients. Unfortunately, there are few effective treatments for hepatitis viral infection. For hepatitis B, anti-viral medicine includes adefovir (Hepsera®), entecavir (Baraclude®), lamivudine (Epivir-HBV®, Heptovir®, Heptodin®), Telbivudine (Tyzeka®) and tenofovir (Viread®). They reduce the ability of the virus to reproduce in the body of the patients and give the liver a chance to heal itself. However, these drugs are not a cure for hepatitis B even though they do reduce the damage caused by the virus. Furthermore, they are needed to be long term use even whole life. For hepatitis C, pegylated interferon or pegylated interferon with ribavirin has been used to treat the disease, the therapeutic efficacy of which are about 40-60%. However, pegylated interferon has unpleasant side effects in many people, such as general weakness, nausea, vomiting and bone marrow suppression. These side effects are so severe that many of the patients cannot continue taking the medication. Overall, these conventional treatments have not been shown to be particularly effective and most are accompanied by significant side effects.

There is a continued need for an effective treatment of hepatitis viral infection, particularly effective in reducing viral titer in a subject infected with a hepatitis virus.

BRIEF SUMMARY OF THE INVENTION

The present invention is based on the unexpected finding that a yolk or yolk antibody obtained from an egg of a fowl which has been immunized using *Helicobacter pylori* as an antigen can significantly reduce viral titer or glutamic oxaloacetic transaminase (GOT)/glutamic pyruvic transaminase (GPT) levels in a subject infected with a hepatitis virus such as HBV or HCV.

Accordingly, the present invention provides a method for treating hepatitis virus infection comprising administering to a subject in need thereof an effective amount of a yolk or yolk antibody obtained from an egg of a fowl which has been immunized using *Helicobacter pylori* as an antigen. In one embodiment, the method is effective in reducing viral titer or GOP/GPT levels in the subject. Particularly, said yolk or yolk antibody as described herein is administered in combination with one or more supplemental ingredients, which may be, for example, (i) a liver protecting agent, (ii) an immunomodulatory agent, (iii) vitamins, (iv) minerals and electrolytes, (v) nutritional supplements, or any combinations thereof.

Also provided is a composition for treating hepatitis virus infection which comprises an effective amount of a yolk or yolk antibody obtained from an egg of a fowl which has been immunized using *Helicobacter pylori* as an antigen. Particularly, the composition further includes one or more supplemental ingredients, which may be, for example, (i) a liver protecting agent, (ii) an immunomodulatory agent, (iii) vitamins, (iv) minerals and electrolytes, (v) nutritional supplements, or any combinations thereof.

The present invention also provides the use of a composition comprising a yolk or yolk antibody obtained from an egg of a fowl which has been immunized using *Helicobacter pylori* as an antigen for the manufacture of a medicament, food additive or health care product for treating hepatitis virus infection, particularly for reducing viral titer or GOP/GPT levels in a patient with hepatitis virus infection. In one embodiment, the composition may further includes one or more supplemental ingredients, which may be, for example, (i) a liver protecting agent, (ii) an immunomodulatory agent, (iii) vitamins, (iv) minerals and electrolytes, (v) nutritional supplements, or any combinations thereof.

The various embodiments of the present invention are described in details below. Other characteristics of the present invention will be clearly presented by the following detailed description about the various embodiments and claims.

It is believed that a person of ordinary knowledge in the art where the present invention belongs can utilize the present invention to its broadest scope based on the description herein with no need of further illustration. Therefore, the following description should be understood as of demonstrative purpose instead of limitative in any way to the scope of the present invention.

BRIEF DESCRIPTION OF THE SEVERAL VIEWS OF THE DRAWINGS

For the purpose of illustrating the invention, there are shown in the drawings embodiments which are presently preferred. It should be understood, however, that the invention is not limited to the embodiments shown.

DETAILED DESCRIPTION OF THE INVENTION

Figure 1:
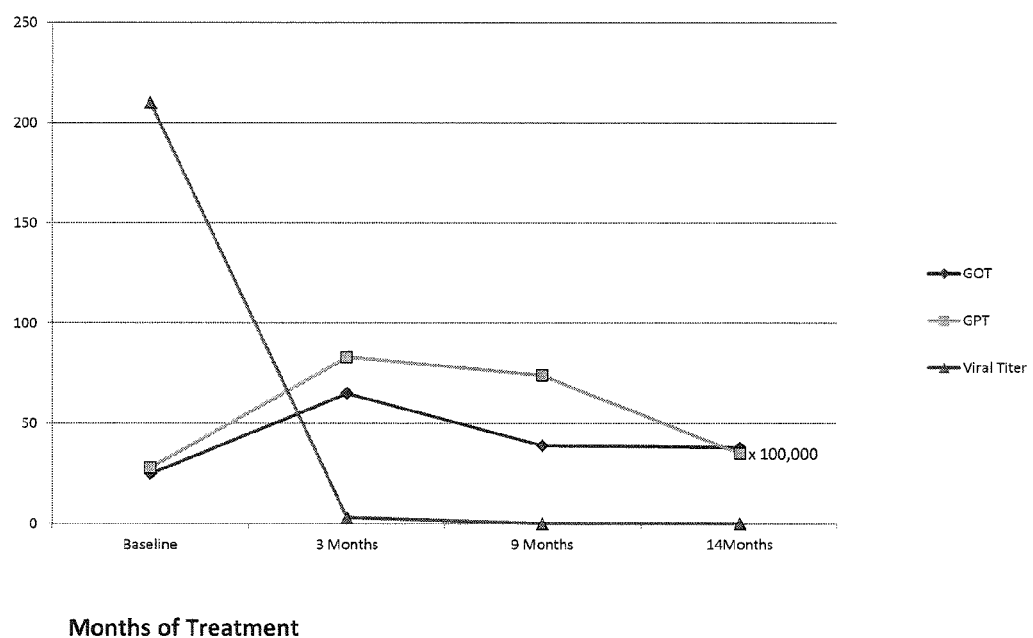
FIG. 1 shows the changes of viral titer and GOT/GPT levels in the case report.

Unless defined otherwise, all technical and scientific terms used herein have the meaning commonly understood by a person skilled in the art to which this invention belongs.

The articles "a" and "an" are used herein to refer to one or more than one (i.e., at least one) of the grammatical object of the article.

Described herein is a method for treating hepatitis virus infection comprising administering to a subject in need thereof an effective amount of a yolk or yolk antibody obtained from an egg of a fowl which has been immunized using *Helicobacter pylori* as an antigen.

The term "treating" a disorder as used herein refers to both therapeutic treatment and prophylactic or preventative measures for the disorder. Those (subjects) in need of treatment include those already with the disorder as well as those in which the disorder is to be prevented. Therefore, the subject to be treated herein may have been diagnosed or determined as having the disorder or may be susceptible or predisposed to the disorder. Hence, treating a subject according to the invention particularly refers to the application or administration of an effective agent or composition to a subject, who has hepatitis virus infection, a symptom of hepatitis virus infection, a predisposition toward hepatitis virus infection, or any disease associated with hepatitis virus infection, with the purpose to cure, heal, alleviate, relieve, alter, remedy, ameliorate, improve, or affect the disease, the symptoms of the disease, the predisposition toward the disease, for example, to inhibit or reduce a hepatitis-associated physical symptom (e.g., jaundice, fatigue, abdominal pain), a hepatitis-associated laboratory finding (e.g., liver enzyme levels in blood or cirrhosis such as glutamic oxaloacetic transaminase (GOT) or glutamic pyruvic transaminase (GPT)), viral replication, or amount (titer) of virus). Reduction of viral titer includes, but is not limited to, decrease or elimination of the virus particles from an infected site or patient. Virus infection can be assessed by any standard approach or method known in the art, including, but not limited to, detection of symptoms, measurement of liver function by laboratory testing, liver biopsy, direct or indirect measurement of liver portal vein pressure, and measurement of virus particles, viral nucleic acid or viral antigen titer and detection and/or measurement of anti-virus antibodies.

"Viral titer" is a term well-known in the art, indicating the amount of virus in a given biological sample. Amount of virus are indicated by various measurements, including, but not limited to, amount of viral nucleic acid; presence of viral particles (such as HBsAg or hepatitis B surface antigen particles); replicating units (RU); plaque forming units (PFU). Generally, for fluid samples such as blood and urine, amount of virus is determined per unit fluid, such as milliliters. For solid samples such as tissue samples, amount of virus is determined per weight unit, such as grams. Methods for determining amount of virus are known in the art and described herein.

"Effective amount" refers to that amount of an agent sufficient to achieve the above-described purpose. Specifically, the amount of the yolk or yolk antibody according to the invention is effective in reducing viral titer and/or GOT/GPT levels in a hepatitis virus-infected subject to be treated. An effective amount can be administered in one or more administrations. The effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art.

The term "subject" as used herein includes human and non-human animals such as companion animals (e.g., dogs, cats, and the like), farm animals (e.g., cows, sheep, pigs, horses, and the like) or laboratory animals (e.g., rats, mice, guinea pigs, and the like).

The term "immunization" as used herein refers to a process known in the art for inducing an immune response in an animal by introducing an antigenic agent or substance into the animal (e.g., by injection, by mucosal challenge, etc.), which preferably results in a specific immune response to the antigenic agent or substance. The antigenic agent or substance can be introduced to the animal, with or without the use of adjuvants.

The term "hepatitis virus infection" as used herein refers to infection of any hepatitis virus known in the art, including but are not limited to those caused by hepatitis A virus (HAV), hepatitis B virus (HBV), hepatitis C virus (HCV), hepatitis D virus (HDV), hepatitis E virus (HEV), hepatitis F virus (HFV), hepatitis G virus (HGV), or cryptogenic hepatitis viruses.

It is unexpectedly found herein for the first time that a yolk or yolk antibody obtained from an egg of a fowl which has been immunized using *Helicobacter pylori* as an antigen is useful for treating hepatitis virus infection, especially reducing the virus titer or the level of GOT or GPT in the patients infected with the hepatitis virus.

*H. pylori* used to prepare the yolk or yolk antibody as used herein can be obtained from a commercial source, such as the American Type Culture Collection (ATCC), which can be the whole bacteria or its antigenic fragment or any combinations thereof. Specifically, the bacteria are cultured for a sufficient period of time, and then harvested, lysed (e.g. by sonication) and centrifuged to obtain a *H. pylori* cell lysate (supernatant). The cell lysate can be mixed with a proper adjuvant as suggested in this art (e.g. a complete Freund adjuvant) and then administered to a fowl via muscle injection, for example, for immunization. Further immunization of a *H. pylori* cell lysate with an incomplete Freund adjuvant, for example, is preferred to boost the immune response in the fowl. In general, one to three times of boost or more is suggested, and the period of time between each immunization is about 7 to 21 days, preferably about 14 days. After the immunization, eggs laid by the fowl are collected and the yolk is isolated from the eggs. Optionally, the yolk is further processed as needed e.g. lyophilized for the purpose of easy storage and subsequent filling in capsules, for example. The presence and titer level of specific antibodies in the yolk can be confirmed by any method such as an immunological assay known in art e.g. Enzyme-linked immunosorbent assay (ELISA) or a method using agglutination reaction. The techniques of immunizing a fowl, harvesting eggs and collecting yolk are well known in the art, such as those described in Shih et al (Clinical and Diagnostic Laboratory Immunology, 9(5): 1061-1066). Examples of fowls as used herein include but are not limited to chickens (hens), ducks, and geese, preferably hens. The applicant's co-pending application, U.S. Ser. No. 12/831, 565, is hereby incorporated by reference in its entirety.

In one embodiment, the method of the invention further comprises administering to the patient one or more supplemental ingredients that impart additional healthful or medicinal benefit. The one or more supplemental ingredients useful herein can be categorized by their healthful benefit or their mode of action, which is merely for the purpose of illustration but not limitation of the invention, because they may provide more than one healthful benefit or operate via more than one mode of action. Specifically, a supplemental ingredient according to the invention can be (i) a liver protecting agent that confers a beneficial advantage in the protection of and/or treatment of the liver, such as mushroom e.g. *Agaricus, Antrodia* (e.g. *Antrodia cinnamomea*), Auricularia, Cordyceps, *Coriolus, Ganoderma, Grifola,* Hericium, *Lentinus,* Pleurotus, *Polyporus,* Poria, *Trametes* and Tremella; milk thistle (*Silybum marianum*); Schisandra (e.g. Schisandra chinensis); Lycium (e.g. Lycium barbarum, Lycium europaeum, and Lycium chinense); Andrographis; artichoke; *Artemisia;* astragalus; Atractylodis Radix; barberry; boldo; bupleurum; Curcumae Radix; dandelion; dong quai (Angelicae Sinensis Radix); fo-ti; fringe tree; fumitory; Ginseng Radix; gotu kola; guggul; kudzu; licorice; neem; Oldennlandiae Hb; *Phyllanthus;* Picrorrhiza; prickly pear; rehmannia; Salviae Miltiorrhiza Radix; skullcap; turmeric; and Zingiberis Radix; (ii) an immunomodulatory agent that can affect one or more or all aspects of the immune response in a subject, such as changing or modifying the number, amount or activity level of components or effector cells (e.g. cytokines, antibodies or natural killer cells) of the subject's immune system, examples of which include but are not limited to prebiotics, probiotics (such as *Lactobacillus* spp. and *Bifidobacterium* spp.), synbiotics, polypore (Phellinus baumii), chitosan, and bee propolis; (iii) vitamins in either natural or synthetic form, such as but are not limited to, vitamin A (e.g., beta carotene, retinoic acid, retinol, retinoids, retinyl palmitate, retinyl proprionate, vitamin B (e.g., niacin, niacinamide, riboflavin, pantothenic acid, etc., vitamin C (e.g., ascorbic acid, etc.), vitamin D (e.g., ergosterol, ergocalciferol, cholecalciferol, etc.), and vitamin E (e.g., tocopherol acetate, etc.); (iv) minerals and electrolytes, such as but not limited to metal salts, chelated minerals, colloidal minerals, colloidal silver, colloidal gold, bentonite, compounds comprising aluminum, arsenic, boron, bromine, calcium (e.g. calcium lactate), chromium, copper, fluoride, germanium, iodine, iron, lithium, magnesium, manganese, molybdenum, nickel, phosphorus, potassium, selenium, selenium, silicon, tin, vanadium, and zinc; and (v) other nutritional ingredients, such as proteins, e.g. milk proteins (casein or whey, or both), soy proteins, or wheat proteins, gelatin, caseinates, grain bran and the like.

Particularly, the yolk or yolk antibody and the supplemental ingredient(s) may be administered either simultaneously (concurrently) or sequentially. The yolk or yolk antibody and/or the supplemental ingredient(s) may be delivered through any medically acceptable route such as orally, parentally (e.g. intramuscularly, intravenously, subcutaneously, interperitoneally), topically, transdermally, by inhalation and the like. Typically, the yolk or yolk antibody and/or the supplemental ingredient(s) is/are orally administered to a subject in need.

To facilitate delivery, the yolk or yolk antibody and the optional supplemental ingredient(s) according to the invention may be, respectively or in combination, formulated into compositions with a physiologically acceptable carrier.

Therefore, the present invention further provides a composition comprising a combination of a yolk or yolk antibody and one or more supplemental ingredients as defined herein. The compositions of the invention can be formulated as a medicament, food additive or health care product.

"Physiologically acceptable" as used herein means that the carrier is compatible with the active ingredient contained in the composition, preferably capable of stabilizing the active ingredient, and not deleterious to the subject to be treated. The carrier may serve as a diluent, vehicle, excipient, or medium for the active ingredient. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The composition can additionally include lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be in any forms as desired using conventional techniques in view of the teachings provided in the specification. In certain examples, the compositions according to the invention can be in the form of tablets, pills, powders, lozenges, sachets, cachets, elixirs, suspensions, emulsions, solutions, syrups, soft and hard gelatin capsules, suppositories, sterile injectable solutions, and packaged powders. In one embodiment, the compositions of the invention are in the form of powders, preferably loaded into capsules.

In one embodiment, the composition of the invention comprises a yolk or yolk antibody as described together with polypore and chitosan, which are particularly present at a ratio of about 2:2:1 by weight.

In another embodiment, the composition of the invention comprises a yolk or yolk antibody as described together with Salviae Miltiorrhiza Radix, Oldennlandiae Hb., Zingiberis Radix, Ginseng Radix, Atractylodis Radix, Curcumae Radix, Angelicae Sinensis Radix, bee propolis, calcium lactate, soy proteins, probiotics (such as *Lactobacillus* spp. and *Bifidobacterium* spp.), and grain bran.

In a further embodiment, the composition of the invention comprises a combination of (a) a first composition comprising the yolk or yolk antibody together with polypore and chitosan, and (b) a second composition comprising Salviae Miltiorrhiza Radix, Oldennlandiae Hb., Zingiberis Radix, Ginseng Radix, Atractylodis Radix, Curcumae Radix, Angelicae Sinensis Radix, bee propolis, calcium lactate, soy proteins, probiotics (*Lactobacillus* spp. and *Bifidobacterium* spp.), and grain bran. In a certain example, the first composition and the second composition are present at a ratio of about 1:0.1-5 (e.g. 1:0.5; 1:1; or 1:1.5) by weight. In another certain example, the first composition comprising the yolk or yolk antibody, polypore and chitosan at a ratio of about 2:2:1 by weight. In still another certain example, the second composition comprising Salviae Miltiorrhiza Radix (5%), Oldennlandiae Hb.(3%), Zingiberis Radix (3%), Ginseng Radix (3%), Atractylodis Radix (2%), Curcumae Radix (1%), Angelicae Sinensis Radix (3%), bee propolis (9.5%), calcium lactate (16.0%), soy proteins (26.5%), and probiotics (5.5%) by weight on the basis of the total weight of the second composition.

The present invention will now be described more specifically with reference to the following embodiments, which are provided for the purpose of demonstration rather than limitation.

EXAMPLE 1

Preparation of Composition of the Invention

A yolk or yolk antibody as used herein was prepared according to a method described in U.S. Ser. No. 12/831,565, which is hereby incorporated by reference in its entirety. Briefly, hens (25 week age, Brown Leghorn hens, n=15) were immunized using *Helicobacter pylori* as an antigen, the eggs were then harvested, and the yolk was removed and lyophilized to obtain yolk lyophilized powders, called "IgY-HP powders," which was then confirmed to have an adequate titer of antibodies for quality control. Powders of polypore and chitosan were purchased from the China Biotechnology Company (Taipei, Taiwan), and mixed with the IgY-HP powder in a ratio of 40% (IgY-HP), 40% (polypore) and 20% (chitosan) (w/w) to obtain IgY-HP combination powders, which were then loaded in capsules (0.48 g per capsule), called "IgY-HP combination capsules."

On the other hand, herbal medicines, Salviae Miltiorrhiza Radix, Oldenlandiae Hb., Zingiberis Radix, Ginseng Radix, Atractylodis Radix, Curcumae Radix, and Angelicae Sinensis Radix, and bee propolis, calcium lactate, soy proteins, and probiotics (*Lactobacillus* spp. and *Bifidobacterium* spp.)

were commercially purchased, mixed together and loaded to capsules, called "herb combination capsules," the composition of which is as follows:

TABLE 1

| Ingredients | 500 mg/capsule (w/w %) |
|---|---|
| Bee Propolis | 9.5% |
| Calcium Lactate | 16.0% |
| Soy Protein | 26.5% |
| Probiotics Combo (comprising *Lactobacillus* spp. and *Bifidobacterium* spp.) | 5.5% |
| Grain Bran | 22.5% |
| *Salviae Miltiorrhiza Radix* | 5% |
| *Oldennlandiae* Hb. | 3% |
| *Zingiberis Radix* | 3% |
| *Ginseng Radix* | 3% |
| *Atractylodis Radix* | 2% |
| *Curcumae Radix* | 1% |
| *Angelicae Sinensis Radix* | 3% |

EXAMPLE 2

Case Reports

Case 1

A 63-year old man received surgery of removal of gallbladder 13 years ago. There was no past history of blood transfusion. His liver function test (GOT, GPT) were persistently high after surgery, and further work-up showed that he was a hepatitis C (HCV) carrier. Since then, he tried a lot of therapies including interferon and anti-viral medicine. However, no much improvement was noted. On Feb. 11, 2009, his HCV was 21,061,891 copies/ml and GOT/GPT were 25/28. Then he started to take four (4) IgY-HP combination capsules and six (6) herb combination capsules per day. Three months later, his HCV titer was 307,332 copies/ml and the GOT/GPT levels were 65/83. Nine months later, his HCV titer was 8,242 copies/ml and the GOT/GPT levels were 39/74. Fourteen (14) months later, his HCV titer was 1,956 copies/ml and the GOT/GPT levels were 38/35. FIG. 1 shows the changes of the virus titer and the GOT/GPT levels in the patient during the 14-month period of time. His symptoms of general weakness were also improved and he is continued to take the capsules of the invention with reduced dose (6 capsules including 3 IgY-HP combination capsules together with 3 herb combination capsules per day).

Case 2

A 45-year old man with past history of blood transfusion when he had traffic accident when he was in high school. About 20 years later, his liver function test (GOT, GPT) were mildly high later and further work-up showed that he was a hepatitis C (HCV) carrier. Because he ran business and had a lot dinner with heavy alcohol intake, he became very tired. His liver function test (GOT, GPT) were moderately high. He received a lot of treatments including acupuncture, and traditional Chinese medicine. However, no much improvement was noted. On May 21, 2009, his HCV was 17,600,000 copies/ml and GOT/GPT were 55/68. Then he started to take four (4) IgY-HP combination capsules and four (4) herb combination capsules per day. Three months later, his HCV titer was 1,500,000 copies/ml and the GOT/GPT levels were 33/42. His symptoms of weakness and poor appetite were also improved and he also gained some weight. He is continued to take the capsules of the invention.

Case 3

A 38-year old man was a hepatitis B (HBV) carrier because his mother was a hepatitis B (HBV) carrier. He was fine until 5 years ago, but then became easy to get tired and dark facial skin when working midnight. His liver function test (GOT, GPT) were noted to be moderately high. He was diagnosed with chronic active hepatitis by his physician. He received some traditional Chinese medicine without much improvement. On Sep. 21, 2009, his HBV was 101,000 copies/ml and the GOT/GPT levels were 55/78. Then he started to take four (4) IgY-HP combination capsules and four (4) herb combination capsules per day. Three months later, his HBV titer was 41,444 copies/ml and the GOT/GPT levels were 35/28. He is energetic and pink facial skin now. He is continued to take the capsules of the invention.

Case 4

A 43-year old woman was a hepatitis B (HBV) carrier because her mother was a hepatitis B (HBV) carrier. She was fine until 5 years ago, but then became easy to get tired. Her liver function test (GOT, GPT) were noted to be moderately high. She was diagnosed with chronic active hepatitis by his physician. Because she ran business and had a lot dinner with heavy alcohol intake, she became very tired. Her liver function test (GOT, GPT) were moderately high. She tried a lot of therapies including anti-viral medicine, and traditional Chinese medicine. However, no much improvement was noted. On Sep. 21, 2009, her HBV titer was 1,802,060 copies/ml and GOT/GPT were 55/78. Then she started to take four (4) IgY-HP combination capsules and four (4) herb combination capsules per day. Three months later, her HBV was 20,850 copies/ml and the GOT/GPT levels were 35/28. She is energetic and pink facial skin now. She is continued to take the capsules of the invention.

Case 5

A 62-year old man was noted to be a hepatitis B (HBV) carrier after the physical check-up. He was easy to get tired. His liver function test (GOT, GPT) were noted to be mildly to moderately high. He received some traditional Chinese medicine without much improvement. On May 2, 2009, his HBV titer was 2,400 copies/ml and the GOT/GPT levels were 65/83. Then he started to take four (4) IgY-HP combination capsules and four (2) herb combination capsules per day. Six months later, his HBV titer was <50 copies/ml and the GOT/GPT levels were 26/29. He is continued to take the capsules of the invention with reduced dose (4 capsules including 2 IgY-HP combination capsules together with 2 herb combination capsules per day).

Case 6

A 48-year old man was noted to a hepatitis B (HBV) carrier after the physical check-up in high school. He was a tannins player and did not fell any general weakness. His liver function test (GOT, GPT) were noted to be mildly elevated. He received some vitamin supplement and traditional Chinese medicine without much improvement. On Nov. 11, 2009, his HBV titer was 770,600 copies/ml and the GOT/GPT levels were 32/78. Then he started to take four (4) IgY-HP combination capsules and four (4) herb combination capsules per day. Seven months later, his HBV titer was 27,700 copies/ml and GOT/GPT were 21/30. He is happy and continues to take the capsules of the invention.

Case 7

A 38-year old man was noted to a hepatitis B (HBV) carrier after the physical check-up in university. His liver function test (GOT, GPT) were noted to be mildly elevated. He received some traditional Chinese medicine without much improvement. On Mar. 26, 2010, his HBV titer was 19,270,000 copies/ml and the GOT/GPT levels were 45/67. Then he started to take four (4) IgY-HP combination capsules and four (4) herb combination capsules per day. Three months later, his HBV titer was 1,117,000 copies/ml and GOT/GPT were 23/35. Six months later, his HBV titer was undetectable (less than 50 copies/nil) and GOT/GPT were 28/345. He is happy and continues to take the half dose of the combination and foloow-up later.

Case 8

A 66-year old lady was noted to a hepatitis C (HCV) carrier during her physical check-up about 10 years. Her liver function test (GOT, GPT) were noted to be moderately elevated for years. She received a lot of vitamin, herbs and other therapies without much improvement. She refused the interferon therapy because afraid of side effect. On Mar. 19, 2010, her HCV titer was 84,400 copies/ml and the GOT/GPT levels were 120/131. Then she started to take four (4) IgY-HP combination capsules and four (4) herb combination capsules per day. One month later, her GOT/GPT were improved to be 84/96. Because her overall condition such as energy, sleeping, G-I systems are much better, she continues to take the same dose of the combination and follow-up 6 months later.

Figure 2:
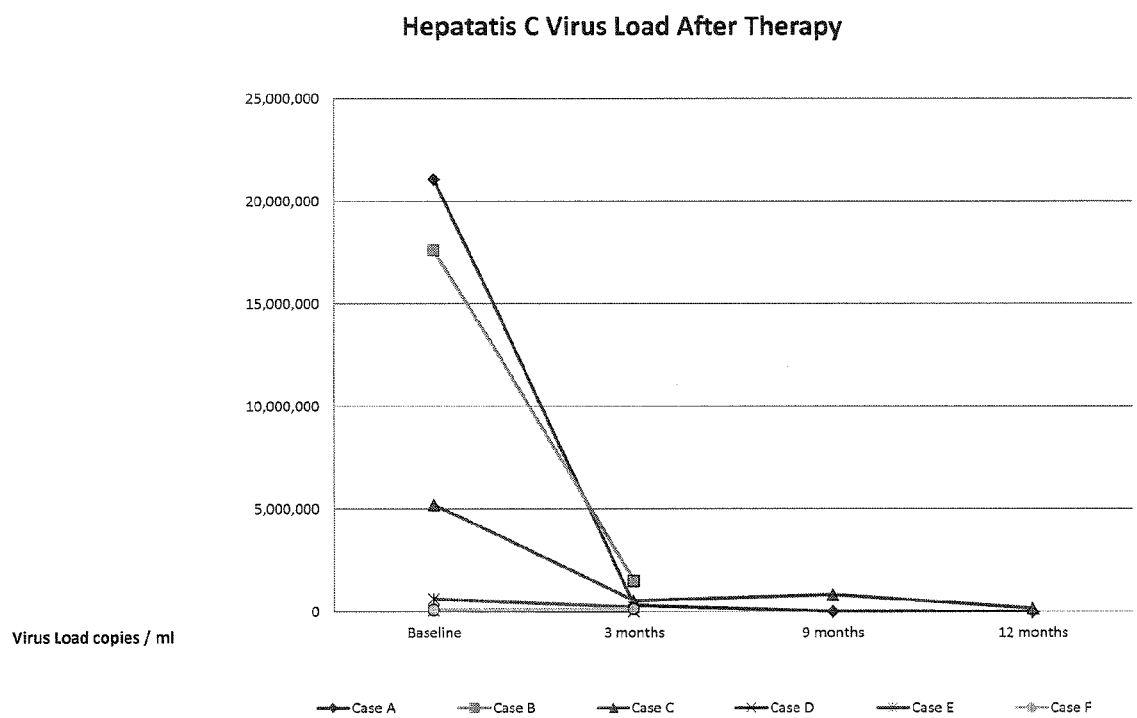
FIG. 2 shows the virus titer of HCV patients before and after administration of the composition of the invention.

In addition, nine (9) hepatitis B carriers and five (5) hepatitis C carriers were included to the clinical trial. They took four (4) IgY-HP combination capsules and four (4) herb combination capsules per day for six to nine months. The serum virus load (copies per ml) of the patients was checked before and after taking this product. Table 1 and Table 2 and FIG. 2 show the results. The results show that the virus titer of the patients was largely reduced after administration of the composition of the invention. In the hepatitis B carriers, at least 50% virus load was decreased, while at least 90% virus load was decreased in the hepatitis C carriers.

TABLE 1

|        | Baseline    | 3 Months   | 6 Months |
|--------|-------------|------------|----------|
| Case 1 | 101,000     | 41,444     | ND       |
| Case 2 | 1,802,000   | ND         | 20,800   |
| Case 3 | 2,400       | ND         | <50      |
| Case 4 | 770,600     | ND         | 27,700   |
| Case 5 | 19,960      | 1,528      | ND       |
| Case 6 | 432,679,000 | 4,148,000  | ND       |
| Case 7 | 225         | <100       | ND       |
| Case 8 | 19,270,000  | 11,170,000 | <50      |
| Case 9 | 50,000      | 500        | ND       |

*ND = not determined.

TABLE 2

|        | Baseline   | 3 months  | 9 months | 12 months |
|--------|------------|-----------|----------|-----------|
| Case A | 21,061,890 | 307,332   | 8,242    | 1,956     |
| Case B | 17,600,000 | 1,500,000 | ND       | ND        |
| Case C | 5,200,000  | 518,000   | 816,000  | 160,400   |
| Case D | 56,000     | 9,800     | ND       | ND        |
| Case E | 610,000    | 215,000   | ND       | ND        |

*ND = not determined.

EXAMPLE 3

Animal Test

Figure 3:
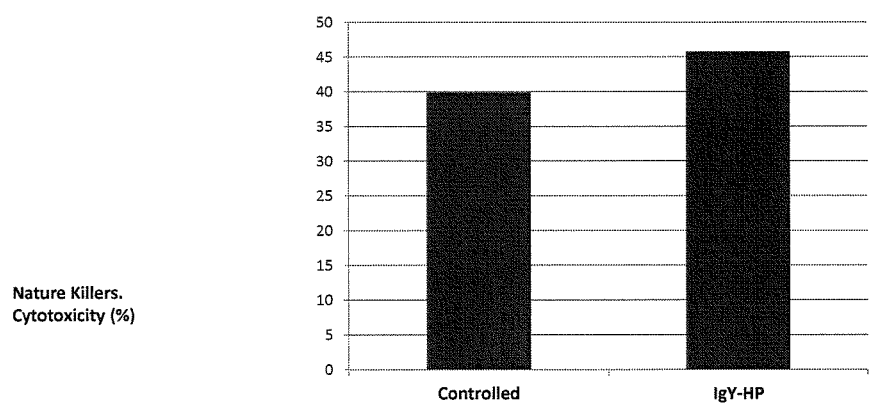
FIG. 3 shows the increase of interferon-gamma resulted from administration of the composition of the invention in the animal test.

The IgY-HP powders obtained in Example 1 was tested in the animal model for its immunological function. The results show that the IgY-HP powders can increase 15% cyto-toxicity of natural killer (NK) cells. Further, it can increase 66% of interferon-gamma when compared with the blank control (FIG. 3). The increase of the NK cell cyto-toxicity and the level of interferon-gamma help the immune system to kill the viruses including HBV and HCV.

Given the above, patients with HBV or HCV infection, after administration of the composition of the invention, exhibited a significantly reduced virus titer (amount) or GOT or GPT level as compared to that prior to administration of the composition of the invention. The composition of the invention is useful for treating hepatitis virus infection.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

I claim:

1. A method for reducing viral titer in a subject infected with hepatitis C virus (HCV) or hepatitis B virus (HBV), comprising administering to the subject a composition comprising (a) a first composition comprising a yolk obtained from an egg of a fowl which has been immunized using *Helicobacter pylori* together with *Phellinus baumii* and chitosan, and (b) a second composition comprising Salviae Miltiorrhiza Radix, Oldennlandiae Hb., Zingiberis Radix, Ginseng Radix, Atractylodis Radix, Curcumae Radix, Angelicae Sinensis Radix, bee propolis, calcium lactate, soy proteins, probiotics, and grain bran, in an amount effective to reduce viral titer in the subject.

2. The method of claim 1, wherein the first composition and the second composition are present at a ratio of about 1:1 by weight.

3. The method of claim 1, wherein the first composition comprises the yolk, *Phellinus baumii* and chitosan at a ratio of about 2:2:1 by weight.

4. The method of claim 1, wherein second composition comprising Salviae Miltiorrhiza Radix (5%), Oldennlandiae Hb.(3%), Zingiberis Radix (3%), Ginseng Radix (3%), Atractylodis Radix (2%), Curcumae Radix (1%), Angelicae Sinensis Radix (3%), bee propolis (9.5%), calcium lactate (16.0%), soy proteins (26.5%), and probiotics (5.5%) by weight on the basis of the total weight of the second composition.

5. The method of claim 2, wherein the first composition comprises the yolk, *Phellinus baumii* and chitosan at a ratio of about 2:2:1 by weight, and the second composition comprises Salviae Miltiorrhiza Radix (5%), Oldennlandiae Hb.(3%), Zingiberis Radix (3%), Ginseng Radix (3%), Atractylodis Radix (2%), Curcumae Radix (1%), Angelicae Sinensis Radix (3%), bee propolis (9.5%), calcium lactate (16.0%), soy proteins (26.5%), and probiotics (5.5%) by weight on the basis of the total weight of the second composition.

6. The method of claim 1, wherein the fowl is a hen.

7. The method of claim 1, wherein the composition is orally administered to the subject.

* * * * *